United States Patent [19]

Kebabian

[11] 4,059,356

[45] Nov. 22, 1977

[54] GAS DETECTOR

[75] Inventor: Paul L. Kebabian, Sommerville, Mass.

[73] Assignee: Environmental Research & Technology, Inc., Concord, Mass.

[21] Appl. No.: 714,115

[22] Filed: Aug. 13, 1976

Related U.S. Application Data

[63] Continuation-in-part of Ser. No. 552,156, Feb. 24, 1975, abandoned.

[51] Int. Cl.$^2$ ............................................. G01N 21/22
[52] U.S. Cl. ..................................... 356/204; 356/51; 356/206; 250/343
[58] Field of Search ................. 356/51, 201, 204, 205, 356/206, 207; 250/339, 343, 349

[56] References Cited

U.S. PATENT DOCUMENTS

| | | | |
|---|---|---|---|
| 3,539,804 | 11/1970 | Billetdeaux et al. | 250/339 |
| 3,547,524 | 12/1970 | Javan et al. | 331/DIG. 1 |
| 3,856,406 | 12/1974 | Noble et al. | 331/94.5 Q |
| 3,860,888 | 1/1975 | Stephens | 250/339 |
| 3,869,613 | 3/1975 | Link et al. | 250/343 |
| 3,893,771 | 1/1975 | Bell | 356/51 |

OTHER PUBLICATIONS

Moore, C. B., "Gas-Laser Frequency Selection by Molecular Absorption," *Applied Optics*, vol. 4, No. 2, Feb. 1965, pp. 252-253.

Bergman, et al., "A New Cascade Laser Transition in He-Ne-Mixture," *Physics Letters*, vol. 29A, No. 2, 7 Apr. 1969, pp. 94-95.

*Primary Examiner*—John K. Corbin
*Assistant Examiner*—R. A. Rosenberger
*Attorney, Agent, or Firm*—Schiller & Pandiscio

[57] ABSTRACT

A methane detector comprising a He–Ne laser in which the plasma tube forms a portion of the resonant cavity and the laser can be stimulated to emit at two different atomic resonances at separate wave numbers $\nu_1$ and $\nu_2$, one of which is more strongly absorbed by methane than the other. Means such as a beam splitter disposed in the resonant cavity, are provided for directing two beams outwardly from the cavity to a pair of detectors each provided in the path of a respective beam. The cavity is tuned so that its length L meets the criterion $m/2L = \nu_1 - \nu_2$, $m$ being a number of half integers. Means are provided for cyclically varying the gain of the laser across one free spectral range through some tuned center value.

20 Claims, 9 Drawing Figures

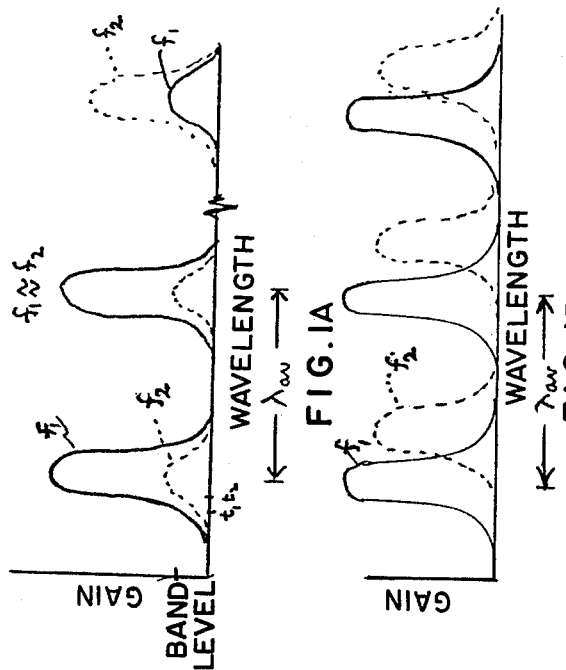
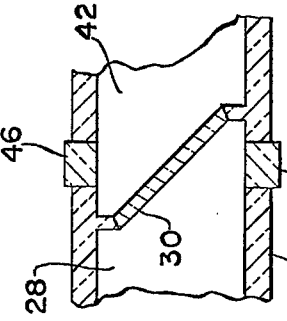
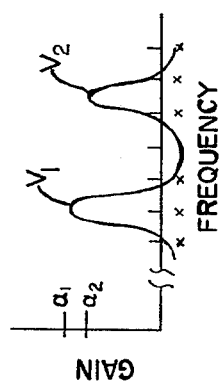
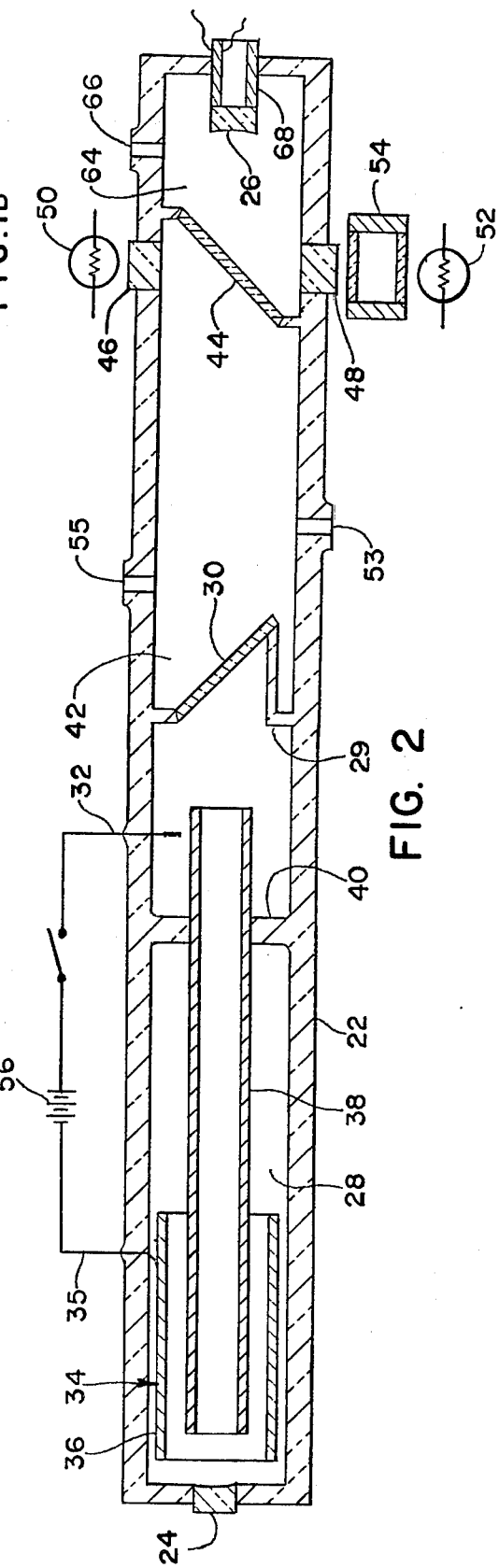

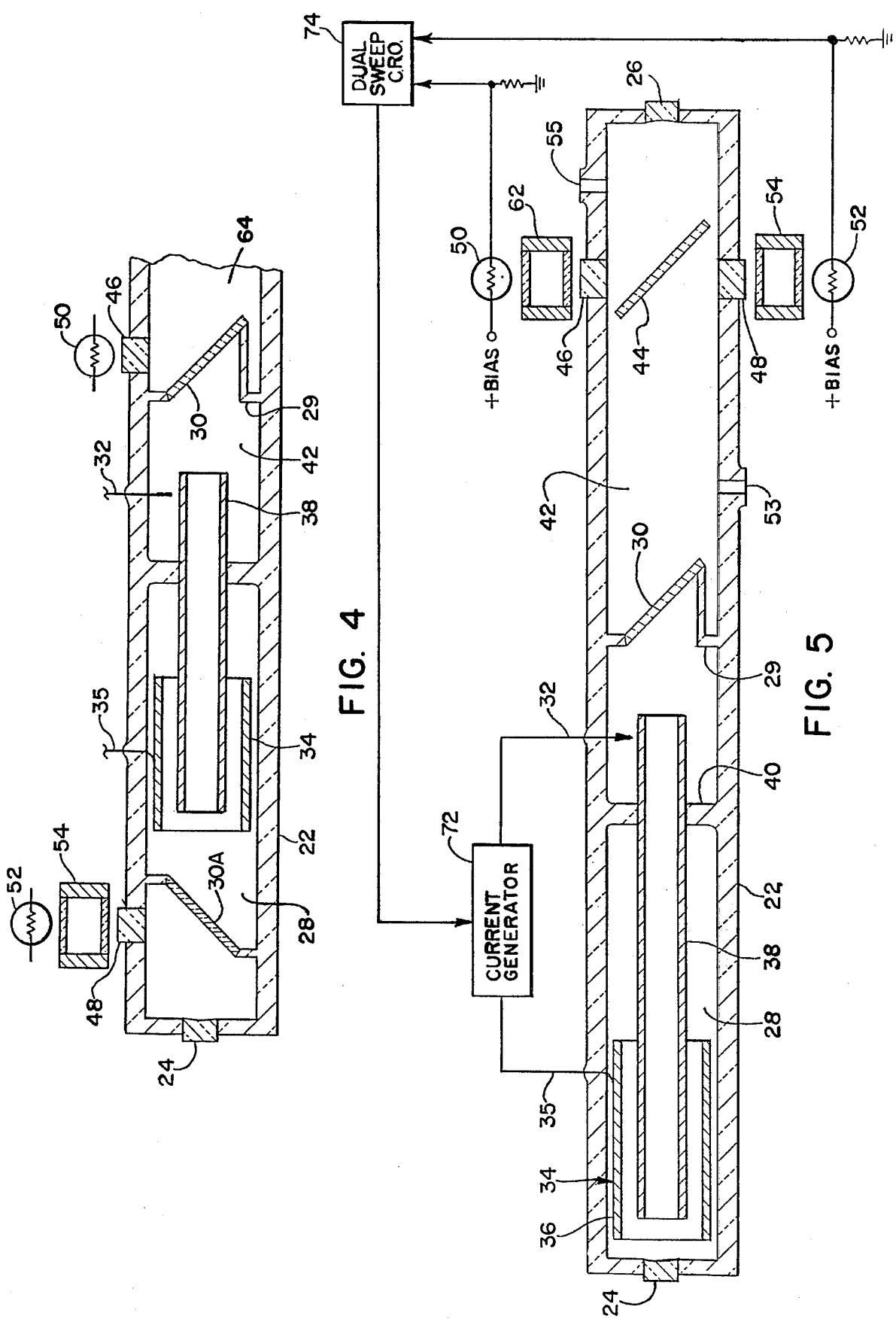

GAS DETECTOR

This is a continuation-in-part of application Ser. No. 552,156, filed 2/24/75, now abandoned.

This invention relates to analytical systems and more specifically to apparatus for the detection and measurement of gases.

In many situations, there is a need to direct or measure the presence or concentration of a specific gas. For example, in mines, there is often a need continuously to monitor for the presence of carbon monoxide, methane or both. In some industrial plants, it is necessary to monitor for the presence of sulfur dioxide, or hydrogen cyanide or the like. Many textile processing factories require careful monitoring of water vapor. Gas monitoring systems are also required in many situations involving the storage and transport of liquified or compressed gases in order to detect and prevent leaks which would otherwise permit dispersion of noxious or lethal materials or result in an unnecessary economic loss.

While a great many systems are employed for gas detection, (e.g. electrochemical detectors, flame photometers, spectrophotometers and the like), they are usually complex, expensive or subject to interference from the presence of gases other than those to be detected.

It is often economically unsound to employ for the detection of a single known gas, a general purpose detector such as a spectrophotometer which is capable of detecting the presence of many different gases. Further, for the purpose of detecting lethal or explosive gases, the detection system should be "fail-safe" and should not be capable of providing an output signal in response to the presence of any other gas likely to be present than that sought to be detected.

The present invention therefore has as its principal object the provision of a simple system for unambiguously and positively indicating the presence of a known gas.

Other objects of the invention will in part be obvious and will in part appear hereinafter. The invention accordingly comprises the apparatus possessing the construction, combination of elements and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings wherein:

FIG. 1 is a plot of gain per unit length against frequency, illustrative of operation of a laser with a particular lasing medium operable at two closely spaced frequencies;

FIG. 1A is a plot of gain against wavelength illustrative of one mode of operation of the present invention;

FIG. 1B is a plot of gain against wavelength illustrative of another mode of operation of the present invention;

FIg. 2 is a schematic diagram partly in longitudinal crosssection of one embodiment of the apparatus incorporating the principles of the present invention;

FIG. 3 is a fragmentary diagram illustrating another embodiment of apparatus incorporating the principles of the present invention;

FIG. 4 is a fragmentary diagram of yet another embodiment of the present invention;

FIG. 5 is a schematic diagram, partly in cross-section of yet another modification of the apparatus of FIG. 2;

Figure 6:
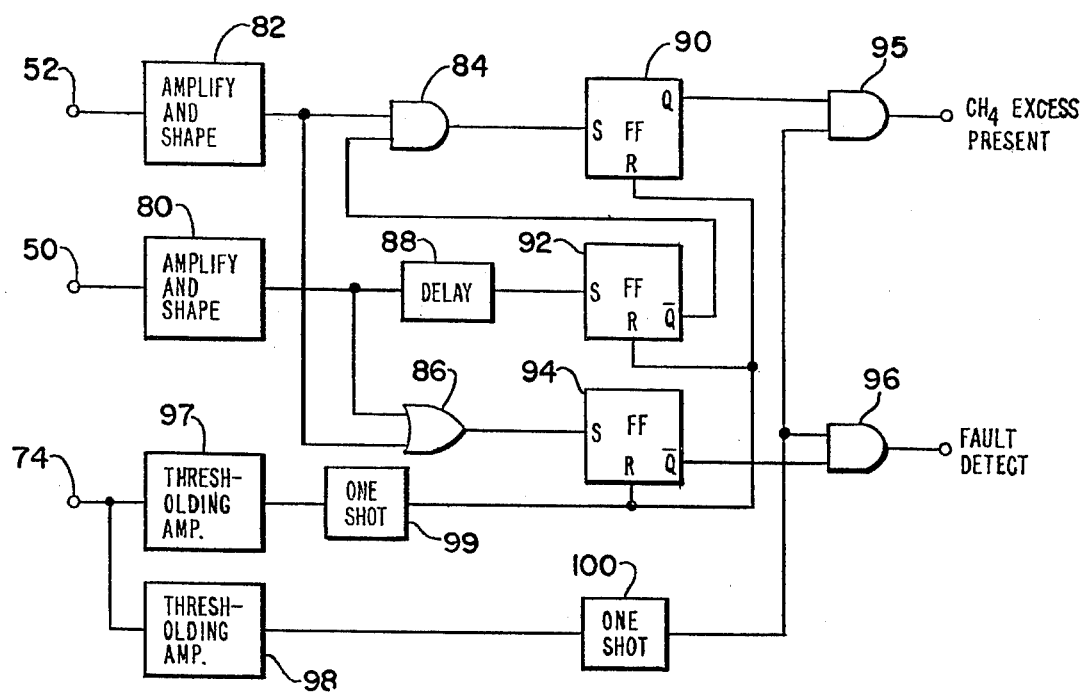
FIG. 6 is a schematic logic circuitry for an element of the apparatus of FIG. 6.

To aid in understanding the parameters and operation of the device, a brief background regarding laser operation may be helpful. Although the term "laser", as used herein may include any device which, by stimulated emission of radiation, provides amplification of an electromagnetic radiation, the laser of principal interest in the neutral gas laser exemplified by the familiar helium-neon laser.

The gas in a neutral gas laser may be excited in a variety of well-known ways (cf. e.g. *CRC Handbook of Lasers*, R. Pressley, Ed., Chemical Rubber Co., Cleaveland, Ohio, 1971). The gain of the lasing medium varies as a function of the frequency of the light being amplified and usually is greatest at several narrow lines or resonance frequencies of the active gas species (e.g. Ne in the case of the He—Ne laser).

When the lasing medium is placed in a resonant cavity of length L and excited, oscillation may occur at one or more of the cavity resonant frequencies (i.e. modes) which for a given transverse field pattern are all approximately spaced apart by a constant frequency difference of $\frac{1}{2}L$ wave numbers. Since for the lasers of interest in the present invention preferably the cavity length $L \gg \lambda$ (where $\lambda$ is a selected resonant wavelength of the active gas species), a small fractional change in L will shift the modes by more than their spacing, while that constant spacing is itself altered by only a small increment.

Associated with each mode of the resonant cavity is a certain loss. For any particular mode, if the net gain (taking account of cavity losses, the gain per unit length of the lasing medium and the length of that part of the cavity containing that medium) is greater than zero decibels, then the time average energy stored in the cavity in that mode will increase. If the net gain is less than zero then the time average energy will decay. If the net gain is zero, a steady state oscillation will occur. Due to saturation, as the energy increases in a mode with gain greater than zero, the gain tends to decrease until the oscillations reach steady state.

For example, with a lasing medium of He-Ne there are two closely spaced resonant frequencies 2947.87 cm$^{-1}$ and 2948.74 cm$^{-1}$; the gain, per unit length, is somewhat greater for the former. These two closely spaced frequencies result from transitions from a single upper state to two different lower states. When the laser oscillates at one of these frequencies, the gain in the other line is reduced.

The present invention is an improvement over a prior art detector for methane gas, which detector was described by C. B. Moore, *Applied Optics*, Volume 4, p. 252 (1965). The physics of the laser system employed in the Moore detector has also been reported by Bergmann et al, *Physics Letters*, Volume 29A p. 94 (1969). These prior art detectors made use of the fact that methane absorbs strongly at 2947.87 cm$^{-1}$, but does not absorb significantly at 2948.74 cm$^{-1}$. As explained by Bergmann et al, in the absence of methane the laser only oscillates at 2947.87 cm$^{-1}$ but when methane is present in the cavity the power output at the latter wave number decreases and that at 2948.74 cm$^{-1}$ increases. This prior art detector suffers from several disadvantages, notably that the relative power outputs at the two frequencies must be measured with high accuracy, the two frequencies must be separated by a spectrometer or similar device and the laser input must use a long tube of consequent great bulk and power consumption.

Most importantly, such prior art methane detectors lack any control over an effect, described hereinafter, which will under some circumstances, degrade accuracy. For simplicity in explanation, consider FIG. 1 which shows an idealized graph of laser gain against frequency. In FIG. 1 the mode spacing is indicated by the indicia marked X on the frequency axis, the indicia being spaced apart by ½L from one another. In laser operation which the graph of FIG. 1 represents, there are two frequencies about which the lasing medium will oscillate to provide the Doppler broadened lines or peaks denoted as $\nu_1$ and $\nu_2$. Note that the mode spacing is substantially greater than the widths of either of the two lines. The gain of the laser at line $\nu_1$ is shown as $\alpha_1$ on the gain axis, the gain of the line $\nu_2$ being shown as $\alpha_2$. If the losses associated with the cavity are slightly less than $\alpha_2 A$ (where A is the active length of the plasma tube) then oscillation is potentially possible at both lines, but can actually occur only in the line centered at $\nu_1$. Neither of the modes near $\nu_2$ has enough net gain to oscillate. Similarly, if the cavity tuning is changed so that one of the modes located near $\nu_2$ moves to the center of the latter line, then oscillation will be possible at $\nu_2$ only even though the line at $\nu_1$ has the larger gain at its center. Thus, it is apparent that a change in the tuning of the laser mimics the effect of a material in the cavity that absorbs at one line but not at the other. A similar effect occurs when a long cavity is used, as in the prior art, so that several modes are located within the width of either line. In such case, undesired changes in cavity tuning, as may be caused simply by changes in temperature, atmospheric pressure, etc., will cause a variation in the relative power outputs at the two frequencies even if there is no change in the composition of the gas in the cavity.

Generally, the present invention relates to a device for detecting the presence of a specific gas, which device includes a laser in which a portion of the resonant cavity contains the material in which a laser emission is stimulated. In one embodiment, another portion of the cavity is ported or vented to admit atmosphere which may contain the gas to be detected. The lasing material is selected so that emission can be stimulated therein at two different atomic resonances or frequencies, one of which is substantially much more strongly absorbed by the specific gas than the other frequency. Means are provided for directing at least a part of the laser beam outward of the cavity. In a preferred form, the latter means are positioned in the laser cavity so as to provide a pair of beams transverse to the direction of resonant radiation propagation in the cavity. Suitably responsive detector means are respectively positioned in those beams, one of which is not responsive to the particular radiant frequency that the specific gas will absorb, and in particular the detector means comprises a gas filter and photoelectric detector.

According to the present invention the cavity length must substantially satisfy the relation $$m/2L = \nu_2 - \nu_1 \quad (1)$$

where $m$ is a number of half integers. Where m is even, the modes in the vicinity of one line have substantially the same spacing relative to its center as those in the vicinity of the other line, regardless of the exact tuning of the cavity. FIG. 1 is illustrative of the case however where m is an odd number. The invention also includes means for scanning or varying the gain of the laser across one free spectral range.

In a first or "synchronous" mode of operation of the invention, the resonant cavity is tuned so that ideally $m$ is an even number of half integers, and then the gain of the lasing medium is continuously scanned or changed so that mode shift occurs through one free spectral range (i.e. by approximately one wavelength around the lines of interest, or in other words, the range of frequencies that can be covered before repetition occurs). During the foregoing scan, either of the two lines of interest can become dominant, depending upon which of the lines possesses the greater gain. If the gain change is achieved by varying the cavity length, it will be appreciated that the change in cavity length is then simply from a half wavelength less (or more) than the cavity length established by equation (1) to a half wavelength more (or less) as the case may be. Whichever of the two resonant frequencies first becomes dominant, in the case of the He-Ne laser tends to suppress the oscillation of the other frequency mode. To approximately equalize static gain at both spectral lines, a bias cell, such as is described hereinafter in connection with FIG. 2 can be employed.

A typical example as shown in FIG. 1A in which wavelength is graphed against gain, indicates that if the cavity length (or tuning voltage or the like which controls gain) is changed, the gain at one frequency $f_1$ will normally rise to some level above broad-band losses at some time $t_1$. The gain at the other frequency $f_2$ will either be suppressed or will rise to some level above broad-band losses at a later but very close time $t_2$. The foregoing is typical of a situation where there is no absorbing gas in the resonant cavity. However, in the presence of the absorbing gas, the relative gains at $f_1$ and $f_2$ will change, and as the cavity length is scanned, the $f_2$ frequency will be dominant and its gain will rise above broad-band losses earlier than the gain rise, if any, at $f_1$. One need only determine which frequency is detected first at the output of the laser to decide whether the gas of interest is present in the resonant cavity. In this mode, both frequencies occur alternatively or approximately simultaneously but not alternately.

Where such scanning takes place in a laser cavity which is tuned so that $m$ in equation (1) is ideally an odd number of half integers, the two resonant frequencies are not "simultaneous" but are quite alternate, i.e. both occur but separately so that gain at one frequency rises to a maximum and then diminishes, and as the laser tuning continues to change, the gain at the second frequency rises to a maximum and then diminishes as shown in FIG. 1B. If the scan of the laser gain is substantially uniformly linear, one can simply time the period during which each oscillation at a specified frequency occurs in proportion to the entire scanning cycle. A comparison of the two fractions of time to obtain a ratio provides a measure of the presence and quantity of the gas of interest. In this latter or "asynchronous" mode of operation, one merely looks at time duration during whichever frequency of interest occurs, and not at laser power output as in the prior art.

Turning now to the drawing there will be seen in FIG. 2 a schematic cross-sectional diagram of the present invention comprising an elonaged hollow glass tube 22 having at opposite ends thereof mirrors 24 and 26 defining between them a Fabry-Perot resonant enclosure. The latter may be optically flat mirrors facing one another, but are preferably confocal spherical mirrors of the type well known in the art. Inasmuch as, in this particular embodiment, it is desired that none of the light stimulated in the Fabry-Perot enclosure be emitted axially, neither of the mirrors should be partially transmitting; instead, both mirrors should be as highly reflective as possible with respect to the particular wavelengths of interest within the device. Additionally, mirrors 24 and 26 can simply be inexpensive aluminized mirrors or the like, thereby eliminating the need for an expensive multi-layer dielectric mirror system to achieve a carefully selected partial reflection and partial transmission as in prior art devices.

A first or plasma tube portion 28 of tube 22 is sealed from the remainder of the interior or tube 22, preferably by barrier 29 which includes a centrally disposed window 30 typically formed of a transparent material set at Brewster's angle with respect to the longitudinal axis of tube 22. Extending through the wall of tube 22 into the interior of portion 28 are a pair of spaced-apart electrodes, such as anode 32 and cathode 34. Anode 32 can be simply a stub of an electrically conductive material preferably having a coefficient of expansion matched to that of the glass. Similarly, the cathode 34 includes lead portion 35 that extends through the wall of tube 22 and is formed of an electrically conductive material having a thermal coefficient of expansion matched to that of the tube wall. Cathode 34 also includes a hollow elongated metallic tube 36 connected to the lead portion 35 and disposed coaxially within portion 28 of tube 22 adjacent mirror 34. An elongated glass discharge tube 38, open at both ends, is disposed within portion 28 of tube 22 extending from within cylindrical portion 36 of cathode 34 to a point adjacent window 20. Means, in the form of a glass septum 40 are provided for supporting tube 38 coaxially within tube 22 and also serves as an insulating barrier preventing an electrical discharge between cathode 34 and anode 32. The interior of plasma tube portion 28 contains gas in which at least two different atomic resonant lines can be caused to lase upon the application of a pumping potential between anode 32 and cathode 34. It will be recognized that the structure thus described is that of a typical DC pumped gas laser well known in the prior art, except that the resonant mirrors are fully reflective and only a portion of the Fabry-Perot enclosure or resonant cavity includes a lasing gas. It will be appreciated that other forms of lasers can also be used, e.g. RF excited, as well.

The analytical device of the present invention further includes, in the remaining portion or chamber 42 of tube 22, beamsplitter 44 disposed across the longitudinal axis of tube 20 so as to divert light from the laser axis into one or more separate beams transverse to the tube axis thereby permitting the use of cavity end mirrors that are fully reflective. To this end, beamsplitter 44 may be, for example, a transparent sheet set at Brewster's angle with respect to the laser axis, one face of the sheet having deposited thereon a thin dielectric layer which will reflect a small portion of axially directed light within tube 22. A number of alternative structures for beamsplitter 44 are equally feasible. The walls of tube 22 on opposite sides of beamsplitter 44 are provided with respective transparent windows 46 and 48 so that light reflected from beamsplitter 44 can be directed from opposite surfaces of the reflecting layer of the latter outwardly from tube 22. It will be appreciated that only a small amount of the light flux within tube 22 need be diverted by beamsplitter 44, so that the latter then does not suppress material laser action.

Positioned adjacent window 46 is a first photoelectric detector 50 which provides an output in the form of an electrical signal in response to the light impinging thereon through window 46.

A similar detector 52 is positioned adjacent window 48. Disposed between window 48 and detector 52 is a selective absorption filter, preferably in the form of gas cell 54 which contains a sufficient quantity of the gas to be detected so as to absorb nearly all of the radiation directed therethrough by beamsplitter 44 at the wavelength of the atomic resonance for which the laser will exhibit, in the absence of any such gas within chamber 42, the highest gain. Other types of filters can of course also be employed or alternatively one can dispense with a separate filter if detector 52 is of the type which is responsive per se only to radiation at the desired wavelength within a narrow passband. Chamber 42 is provided with inlet and outlet ports 53 and 55 so that an atmosphere in which the presence of a particular gas is sought to be detected, may be introduced into and withdrawn from chamber 42 if desired.

As noted, the Moore detector functions by comparing the power outputs at two laser frequencies, one of which is absorbed the other of which is not absorbed by the gas to be detected, when samples of the gas under test are introduced into the laser resonant cavity. Additionally, such a comparison of powers necessarily requires relatively high precision in their measurement and the cost of the system is thus increased because stable and accurate detectors and electronic components must be used.

The present invention may include within the resonant cavity of the laser, a sample, inside transparent bias cell 64, of a material having predetermined different radiation absorption characteristics at the two laser frequencies, thereby tending to equalize static gain at the two lines. The absorbent material in cell 64 may be a gas or other material with suitable absorption characteristics. It should be noted that, in FIG. 2, cell 64 is conveniently formed by using beamsplitter 44 as a wall thereof to seal off a portion of chamber 42 adjacent mirror 26. Filling port 66 is thus provided to permit cell 64 to be filled with an appropriate concentration of a desired radiation absorbent material.

In any laser, there exists a variety of ways by which the gain of the laser medium, at the cavity mode frequencies, may be varied. In particular, the current by which the laser medium is excited may be varied. Also, provided that the spacing between modes is substatially greater than the Doppler line widths, the gain may be varied by slightly changing the cavity length, thereby shifting the locations of the modes with respect to the line centers. It will be appreciated that in this latter case, the previously noted condition regarding cavity length must be substantially satisfied, if the gains for the modes in the vicinity of each line are to vary in substantially the same way. This variations in cavity length may be achieved in a variety of manners, such as is shown in FIG. 2 wherein cavity mirror 26 is mounted on piezoelectric element 68 and oscillation of the latter in known manner then cyclically varies the gain at the two laser frequencies. Alternatively, one can vary cavity length by mounting the mirror on an element, the length of which is changed by varying its temperature, or by varying the pressure of the atmosphere in part of the cavity, thereby changing the refractive index and the optical (but not the physical) length of the cavity.

In an alternative embodiment of the device, shown only in fragment in FIG. 3, window 30 which serves to physically separate plasma tube 28 from chamber 42, also constitutes a beamsplitter and thus windows 46 and 48 are located adjacent window 30. Because this latter alternative requires that window 48 which is in plasma tube 28 be vacuum tight, in yet another embodiment of the device, shown only in fragment in FIG. 4, plasma tube 28 is provided with angled windows 30 and 30A at opposite ends, each of such windows constituting a beamsplitter so that window 47 is located adjacent window 30 and window 48 is located adjacent window 30A. This latter structure eliminates the need for a vacuum-tight window in the wall of the plasma tube. Both the embodiments of FIGS. 3 and 4 of course employ dual detectors with either one or two filters, but for brevity neither detectors nor filter are shown.

The operation of the system of FIG. 2 can advantageously be described in connection with some exemplary parameters. For example, the device of FIG. 2 can be used to detect the presence of methane gas by the absorption of light at a wavelength of 3.3913 $\mu$ (in air). In order to provide such a line as the dominant emission of a laser, one can use a helium-neon mixture as the lasing gas in portion 28 of tube 22. A system which produces this wavelength as a strong oscillation is described in the above-cited articles wherein the authors point out that if the 3.3913$\mu$ line is suppressed by methane absorption, a transition at 3.3903$\mu$ begins to oscillate.

For operation in the synchronous mode, the cavity length between mirrors is tuned so that $m$ in equation (1) is an even number of half integers. Portion 28 of the device of FIG. 2, provided with an appropriate lasing gas mixture, is then subjected to appropriate power applied across electrodes 28 and 34 from power source 56, and mirror 26 is continuously scanned over a free spectral range, i.e. from at least half an average wavelength of the laser oscillation to preferably a full such wavelength. As noted earlier, if no absorbing gas is in cavity 42, the laser will oscillate at a first or dominant mode, suppressing the other. But in the presence in cavity 42 of a gas absorbant for the dominant frequency, as the mirror scans, the gain at the second frequency will rise more quickly than for the first frequency so the second frequency oscillations will suppress the first.

For example, assume that filter 54 is filled with methane, hence detector 52 will respond to all the laser emissions except the 3.3913$\mu$ line and thus will detect the presence of any emissions at 3.3903$\mu$. Detector 50 will then be responsive to both lines (assuming no filter for detector 50). In the absence of methane in cavity 42, the laser oscillates at the 3.3913$\mu$ line, as the mirror scans and only detector 50 will therefore provide an output. But when absorbing methane is present in cavity 42, subsequent scanning causes the 3.3903 $\mu$ line to dominate and both detectors 50 and 52 will provide output signals which can of course be displayed or read-out on known devices.

For asynchronous operation, the cavity is tuned so that $m$ is an odd number of half integers, lasing creates a comb of frequencies which are generally more widely spaced than the line widths. One of the frequencies will be close enough to a line center to have appreciable gain. By varying the cavity length by scanning mirror 26 over a free spectral range, one varies the spacing between resonant frequencies of the laser cavity, so that both lines of interest appear at the respective detectors but alternately. The time relation of appearance of the two lines is a function of absorbant gas concentration in cavity 42.

Note that these systems do not require an accurate power measurement or comparison. All that must be determined is the existence or nonexistence of oscillation at one of the two lines of the laser medium or the time relation between oscillation at the lines.

Referring now to FIG. 5 there will be seen an alternative form of the present invention which includes a structure similar to that of FIG. 2 including all the elements housed in tube 22. The device also includes a pair of detectors 50 and 52 and associated filters 54 and 62 positioned adjacent output windoes 46 and 48 through which the light from internal beamsplitter 44 is diverted. However, in distinction to the system heretofore described in connection with FIG. 2, the device of FIG. 5 includes other means for varying the laser gain. This latter means is exemplified by variable current generator 72 controlled by a ramp or saw tooth oscillator (such as the sweep generator of cathode ray oscilloscope 74) so that the current from the generator periodically rises, for example linearly, with time from a predetermined minimum to a predetermined maximum.

Coupled to the output of detectors 50 and 52 in FIG. 5 are means, here shown as dual trace oscilloscope 74, the indicating the existence of oscillation at the two laser lines. As the gain is scanned by the oscillator the observer decides at which line oscillation first occurs in time by noting on which trace a signal first appears. The observer may also note if no oscillation at all occurs, in which case a system failure is indicated. Thus, the system is "fail-safe" in the sense that failure of the laser tube (by far the most probable failure mode of such a system) is indicated by the absence of oscillation.

The above decision making process by the observer may be equally well done automatically, by the circuitry shown in FIG. 6, in which 52, 50 and 74 denote respectively, input terminals connected to the outputs of respectively detector 52, detector 50 and the sweep source used to control the current generator.

In FIG. 6, the outputs of detectors 50 and 52 are shown at corresponding terminals each respectively connected to the input of known amplification and wave or pulse shaping circuitry 80 and 82 respectively. The output of circuit 82 connected to one input of AND gate 84 and also to an input of OR gate 86. The output of circuit 80 is connected as another input to OR gate 86 and is also connected as an input to a delay circuit such as delay line 88. The output of gate 84 is connected to the set input of RS type flip-flop 90. Similarly, the outputs of delay line 88 and of gate 86 are respectively connected to the set inputs of RS flip-flop 90. Similarly, the outputs of delay line 88 and of gate 86 are respectively connected to the set inputs of RS flip-flops 92 and 94. The Q output of flip-flop 92 is connected as another input to AND gate 84. The Q output terminal of flip-flop 90 is connected as one input to AND gate 95. The Q output terminal of flip-flop 94 is connected as an input to AND gate 96. The output of saw tooth oscillator of oscilloscope 74 of FIG 5 is connected as an input to threshholding amplifiers 97 and 98. The output of threshholding amplifier 98 is connected to the input multivibrator or one-shot 100 and the output of the latter is connected as an input to both gates 95 and 96. The output of amplifier 97 is connected to the input of monostable multivibrator or one-shot 99, the output of the latter being connected to each of the reset terminals of flip-flops 90, 92 and 94.

Threshholding amplifier 97 has a very low threshhold, and at or immediately after the start of each cycle of the sawtooth, it triggers one-shot 99, thereby resetting all the RS flip-flops in the circuit. The threshholding amplifier 98 has a high threshhold, and at the end of the increasing phase of thw sawtooth, it triggers one-shot 100, which transmits a pulse to AND gates 95 and 96. These gates will transmit that pulse if their respective other inputs are high; a pulse transmitted by gate 95 may trigger an alarm device, not shown, such as a bell, to indicate an excess of $CH_4$ or other gas, and likewise a pulse transmitted by 96 may trigger a system fault alarm.

The signals from detectors 52 and 50 are amplified and clipped in amplifiers 82 and 80, respectively; if either of the laser lines oscillates, at least one of the outputs of amplifiers 82 and 80 will go high, thus causing the output of OR gate 86 to go high. This sets flip-flop 84, this preventing the pulse from one-shot 100 from being transmitted by gate 96. On the other hand, if no oscillation has occurred, gate 96 transmits, and a fault is thus signalled.

The case of no-oscillation has been considered above. When the laser oscillates there are two alternative situations: a signal from detector 50 only, indicating that the gas concentration does not exceed the threshhold, or a signal from both 50 and 52, when the gas concentration does exceed the threshhold. When the gas to be detected is $CH_4$, then cell 54 contains $CH_4$, detector 52 responds to light at 3.3903μ only, and detector 50 responds to light at both 3.3903μ and at 3.3913μ (assuming that cell 62 is not used).

When a signal is received from detector 50 only, it is transmitted through delay element 88 and sets RS flip-flop 92. One input to AND gate 84 is low, and so subsequently arriving signals from detector 52 are not transmitted to RS flip-flop 90. The latter stays reset and thereby prevents gate 95 from transmitting the pulse from one-shot 100.

When oscillation first occurs at the wavelength not absorbed by the gas to be detected (i.e. 3.3903μ in the case of $CH_4$), signals are generated approximately simultaneously by detectors 52 and 50. This simultaneity may not be exact, due to individual variations between detectors. Delay element 88 is selected so that a signal reaches flip-flop 90 before one reaches flip-flop 92, in spite of the above variations. Because flip-flop 90 is set, gate 95 transmits a pulse to warn of the gas concentration threshholding being exceeded.

The above description thus shows how the required decision can be carried out automatically when the gain is varied by sawtooth modulation of the laser current. With other gain variation methods, or when cell 62 is used, appropriately modified logic circuitry will similarly implement the necessary decisions.

Figure 7:
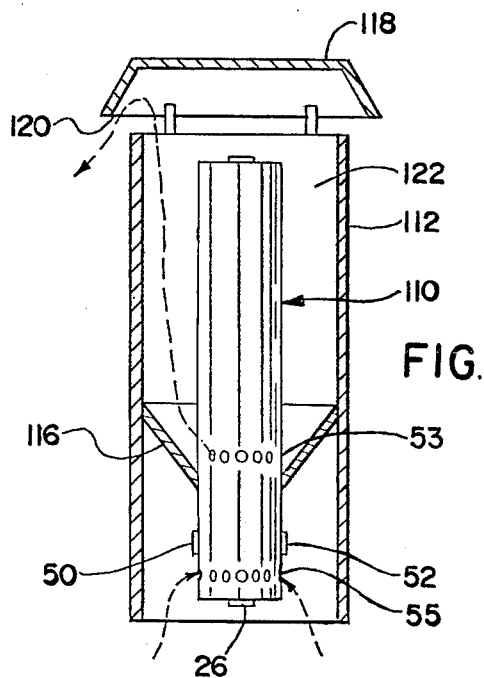
FIG. 7 is a cross-sectional elevational view of a detection system employing the apparatus of either FIGS. 2 or 6.

Advantageously, the detector mechanism of the present invention in a practical embodiment can be produced in a very simple form such as shown in FIG. 7 in which an instrument, for example such as that of FIG. 2 or FIG. 5, identified by the reference numeral 110 is shown disposed in a position wherein the long axis of the system is aligned in a vertical direction approximately with respect to the earth's center. Device 110 is provided with a plurality of input ports 55 disposed below another plurality of output ports 53. Device 110 is supported axially within open-ended cylindrical housing 112 and is spaced apart from the housing so as to provide annular interspace 114. Baffle or conical barrier 116 is provided between housing 112 and device 110 so as to prevent the free flow of air directly through interspace 114 from one end of housing 112 to the other. Barrier 116 is connected or sealed to device 110 circumferentially about the latter at a position intermediate ports 53 and 55. If desired, the device of FIG. 7 can be provided with a top or loosely fitting can 118 mounted so as to provide a substantially annular space 120 through which gas can move from the upper portion of interspace 114.

The operation of device 110 in FIG. 7 is substantially as described heretofore in connection with the embodiments of FIG. 2 or 5. However, it will be apparent that a substantial amount of heat is generated in plasma tube 28 (not shown) in device 110. The thermal energy causes expansion of gas within the adjacent portion 122 of interspace 114, and as the heated gas (shown in dashed line) rises, air will be drawn through ports 55 and then ce proceed out through ports 53 into interspace portion 122 and out through space 120. The gas exhaust from space 120 serves to draw fresh cooler atmosphere into chamber 42 direction approximately with respect to the earth's center. Device 110 is provided with a plurality of input ports 55 disposed below another plurality of output ports 53. Device 110 is supported axially within open-ended cylindrical housing 112 and is spaced apart from the housing so as to provide annular interspace 114. Baffle or conical barrier 116 is provided between housing 112 and device 110 so as to prevent the free flow of air directly through interspace 114 from one end of housing 112 to the other. Barrier 116 is connected or selaed to device 119 circumferentially about the latter at a position intermediate ports 53 and 55. If desired, the device of FIG. 12 can be provided with a top or loosely fitting cap 118 mounted so as to provide a substantially annular space 120 through which gas can move from the upper portion of interspace 114.

The operation of device 110 in FIG. 7 is substantially as described heretofore in connection with the embodiments of FIG. 2 or 5. However, it will be apparent that a substantial amount of heat is generated in plasma tube 28 (not shown) in device 110. The thermal energy causes expansion of gas within the adjacent portion 122 of interspace 114, and as the heated gas (shown in dashed line) rises, air will be drawn through ports 55 and thence proceed out through ports 53 into interspace portion 122 and out through space 120. The gas exhaust from space 120 serves to draw fresh cooler atmosphere into chamber 42 through ports 55. The device of the invention by virtue of the coaxial housing 112, and barrier 116 and its own heat, thus serves as its own air pump for continuously sampling the ambient atmosphere.

For example, although the embodiments thus described use fully reflective end mirrors to bound the resonant cavity of the laser and thus also use internal beamsplitters, alternative embodiments can provide at least one of the desired external laser beams through a standard end mirror partially transmissive to the laser radiation, and thus can achieve beamsplitting either by using an external beamsplitter in the path of the axial beam from a partially transmissive end mirror or by using a pair of such partially transmissive end mirrors.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A device for detecting the presence of a specific gas in an atmosphere to be tested, said device comprising, in combination:

a laser having a resonant cavity at least a portion of which contains a material in which emission can be stimulated at least at two different frequencies centered at wave numbers separated by some difference $\Delta v$, the emission at one of said frequencies being more strongly absorbed by said gas that the emission at the other of said frequencies, said material and cavity being selected so that the gain of said laser is normally higher for emission at said one frequency that at said other frequency, said cavity being tuned so that $$m/2L = \Delta v$$

where L is the optical length of the cavity and $m$ is a number of half integers, means for directing at least part of the stimulated emission outwardly from said cavity, first detector means positioned for irradiation by said part of said emission for producing electrical signals responsively to emissions at least at said other frequency; and means for cyclically varying the tuning of said laser through at least a free spectral range.

2. A device as defined in claim 1 wherein said means for directing comprises means for dividing said emission into two beams.

3. A device as defined in claim 2 wherein said detector means comprises first and second photoelectric detectors positioned to be irradiated by respective ones of said two beams, said first and second detectors being respectively responsive to emissions at different ones of said frequencies.

4. A device as defined in claim 3 including means coupled to said detectors for determining a ratio of the time duration during which each of said first and second detectors is respectively irradiated by excitation wavelengths.

5. A device as defined in claim 2 wherein said detector means comprises a first photoelectric detector and a first filter interposed in the path of one of said beams so as to absorb radiation at said one frequency.

6. A device as defined in claim 5 wherein said first filter comprises a gas cell containing sufficient of said gas to absorb radiation at said one frequency in said one beam so that substantially none of said radiation at said one frequency can be detected by said first detector.

7. A device as defined in claim 5 wherein said detector means also comprises a second photoelectric detector and a second filter interposed in the path of the second of said beams so as to absorb radiation at least at said other frequency.

8. A device as defined in claim 7 wherein said second filter comprises a cell containing sufficient material which absorbs radiation at said other frequency so that substantially none of said radiation at said other frequency can be detected by said second detector.

9. A device as defined in claim 2 wherein said means for dividing comprises beam splitting means for directing said first beam in a first direction substantially transversely of the direction of resonant propagation in said cavity and for directing said second beam in a second direction substantially transversely of the direction of resonant propagation in said cavity.

10. A device as defined in claim 9 wherein said beam splitting means is disposed within said cavity.

11. A device as defined in claim 10 wherein said beam splitting means comprises a window dividing said one portion of said cavity from said second portion.

12. A device as defined in claim 10 wherein said beam splitting means comprises a pair of windows defining respective ends of said one portion of said cavity.

13. A device as defined in claim 1 wherein said resonant cavity is bounded at opposite ends by mirrors which are substantially not transmissive to radiation at either of said frequencies.

14. A device as defined in claim 1 including a bias cell disposed within said cavity in the path of resonant radiation propagation and containing materil which absorbs enough of said emission at said one frequency to approximately equalize gains at line centers of said frequencies.

15. A device as defined in claim 1 wherein said means for varying the gain of said laser comprises a pair of opposed mirrors bounding said resonant cavity, at least one of said mirrors being mounted for movement with respect to the other.

16. A device as defined in claim 1 including means coupled to said detector means for determining the relative time at which the laser provides oscillations at each of said two frequencies during each cycle of variation of gain.

17. A device as defined in claim 16 wherein said means for determining said relative time comprises a dual-sweep cathode ray oscilloscope.

18. A device as defined in claim 17 wherein a second portion of said cavity includes means for admitting said atmosphere into said second portion, and wherein said means for determining said relative time comprises a logic circuit for producing a signal when said relative time indicates that a minimum threshhold of concentration of said specific gas in the atmosphere admitted to said second portion has been exceeded.

19. A device as defined in claim 1 wherein a second portion of said cavity includes means for admitting said atmosphere into said second portion, said device including means for producing a flow of said atmosphere through said second portion of said cavity.

20. A device as defined in claim 1 wherein said cavity is defined, at least in part, by an elongated envelope, which includes a second portion of said cavity having input ports adjacent one end of said envelope and output ports disposed at a position intermediate said input ports and the other end of said envelope, said device including an open-ended tubular housing said envelope being disposed substantially coaxially within said housing and spaced there from, said input ports being adjacent one open end of said housing and;

barrier means coupled between said housing and a portion of said envelope intermediate said input and output ports for obstructing gas flow through the interspace between said envelope and housing.

* * * * *